United States Patent

Kanai

[11] Patent Number: 5,158,529
[45] Date of Patent: Oct. 27, 1992

[54] PUMPING DEVICE FOR OPERATING AN INTRA-AORTIC BALLOON

[75] Inventor: Naritoshi Kanai, Anjo, Japan

[73] Assignees: Aisin Seiki Kabushiki Kaisha, Kariya; Kabushiki Kaisha Shinsangyokaihatsu, Tokyo, both of Japan

[21] Appl. No.: 675,947

[22] Filed: Mar. 27, 1991

[30] Foreign Application Priority Data

Mar. 29, 1990 [JP] Japan ................... 2-82453

[51] Int. Cl.$^5$ .......................... A61N 1/362
[52] U.S. Cl. .................................. 600/18
[58] Field of Search ............ 128/672, 673, 675; 600/17, 18; 604/96, 99

[56] References Cited

U.S. PATENT DOCUMENTS

| | | | |
|---|---|---|---|
| 3,769,960 | 11/1973 | Robinson | 600/18 |
| 3,985,123 | 10/1976 | Herzlinger et al. | 600/17 |
| 4,672,974 | 6/1987 | Lee | 128/673 |
| 4,692,148 | 8/1987 | Kantrowitz et al. | 604/96 |
| 4,733,652 | 3/1988 | Kantrowitz et al. | 128/672 |
| 4,794,910 | 1/1989 | Mushika | 600/18 |
| 4,796,606 | 1/1989 | Mushika | 600/18 |
| 4,809,681 | 3/1989 | Kantrowitz et al. | 600/17 |
| 4,832,005 | 5/1989 | Takamiya et al. | 600/18 |
| 4,901,735 | 2/1990 | von Berg | 128/673 |
| 4,974,774 | 12/1990 | Nakagawa et al. | 600/18 |

FOREIGN PATENT DOCUMENTS

62-189049 8/1987 Japan .

Primary Examiner—William E. Kamm
Assistant Examiner—J. Jastrzab
Attorney, Agent, or Firm—Burns, Doane, Swecker & Mathis

[57] ABSTRACT

A device for operating an intra-aortic balloon pump having an arterial pressure sensor associated therewith for measuring arterial pressure includes a pressure sensor for measuring an internal pressure of the balloon pump and an arrangement for applying a positive pressure in order to provide fluid to the balloon pump for purposes of inflating the ballon pump. An adjustment device is also included for adjusting the zero point of the arterial pressure sensor. The adjustment device compares the arterial pressure measured by the arterial pressure sensor with the internal pressure of the balloon pump as determined by the pressure sensor and adjusts the zero point accordingly to eliminate differences between the arterial pressure and internal pressure.

11 Claims, 6 Drawing Sheets

PUMPING DEVICE FOR OPERATING AN INTRA-AORTIC BALLOON

FIELD OF THE INVENTION

The present invention pertains to a device for use in conjunction with an intra-aortic balloon pump. More particularly, the present invention concerns a device for driving/operating an intra-aortic balloon pump that has an arterial pressure sensor associated therewith.

BACKGROUND OF THE INVENTION

Electrocardiograms or arterial pressure signals have long been helpful in the treatment of patients when used in conjunction with intra-aortic balloon pumps. Japanese Patent Publication No. 62-189049 (1987) discloses one example of how arterial pressure signals can be obtained. As described in that publication, an arterial pressure sensor is set in place at the tip of the intra-aortic balloon pump.

However, when an arterial pressure sensor is set at the tip of the intra-aortic balloon pump, the intra-aortic balloon pump and the sensor are inserted completely into the patient's body. As a result, it is difficult to keep the pump properly calibrated by appropriately maintaining the zero point of the sensor. Therefore, with conventional devices, the zero point gradually fluctuates, thereby preventing users from accurately detecting arterial pressure. This is a problem that has been noted with conventional devices of the aforementioned type.

Other types of intra-aortic balloon pumps are disclosed in U.S. Pat. Nos. 4,692,148; 4,733,652; 4,794,910; 4,796,606; 4,809,681; and 4,832,005.

SUMMARY OF THE PRESENT INVENTION

In light of the foregoing discussion, it can be seen that known types of balloon pumps are susceptible to certain improvements. As a result, the present invention was designed to provide a device that makes it possible to adjust the zero point of the arterial pressure sensor after it has been inserted into the aorta and during use.

To achieve the foregoing advantage, the present invention includes an arterial pressure sensor which is set in place at the tip of an intra-aortic balloon pump, a pressure sensor associated with the balloon pump for measuring the internal pressure of the balloon pump, means for applying a positive pressure to supply a gas in a substantially uniform amount to the balloon pump to thereby inflate the balloon pump, and an adjuster for comparing the arterial pressure measured by the artery sensor with the internal pressure of the balloon pump detected by the pressure sensor, and thereafter adjusting the zero point of the arterial pressure sensor so as to eliminate any difference between the arterial pressure and the internal pressure of the balloon pump.

By the present invention, the proper amount of gas is supplied to the balloon pump through the application of pressure, and, consequently, the balloon pump is inflated. During that time, the balloon pump will continue to inflate until the internal pressure of the balloon pump is the same as the arterial pressure. When the internal pressure and the arterial pressure are substantially equal, inflation of the balloon pump ceases. Once the inflation of the balloon pump has stopped, the internal pressure of the balloon pump and the pressure of the artery will be the same. When conditions are at that state, the adjuster will compare the arterial pressure with the internal pressure of the balloon pump, adjust the zero point of the arterial pressure sensor accordingly.

BRIEF DESCRIPTION OF THE DRAWINGS

The features of the device according to the present invention for operating/driving a balloon pump having an arterial pressure sensor will become apparent from the description bellows, considered in conjunction with the accompanying drawing figures in which like elements bear like reference numerals and wherein.

DETAILED DESCRIPTION O THE PREFERRED EMBODIMENT

Figure 3:
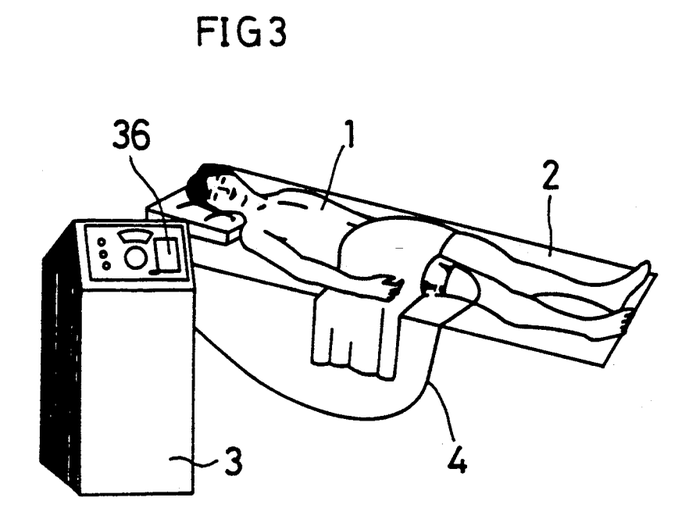
FIG. 3 is a perspective view illustrating a patient being treated with a balloon pump, and including a device according to the present invention for driving the balloon pump.

Referring initially to FIG. 3 which depicts a patient 1 lying on a hospital bed 2 and being treated with an intra-aortic balloon pump (hereinafter referred to as a "balloon pump"), as the device 3 for driving the balloon pump 4 (hereinafter referred to as the "driver") is placed near the hospital bed 2. The balloon pump 4 can be introduced into the aorta via the patient's femoral artery. Since there are various methods known in the field for implanting the balloon pump 4 into the body of a patient 1, a discussion of such method is not included herein. However, by way of example, it is to be noted that the seldinger method can be utilized to insert the balloon pump 4 into the body of the patient 1.

Figure 1:
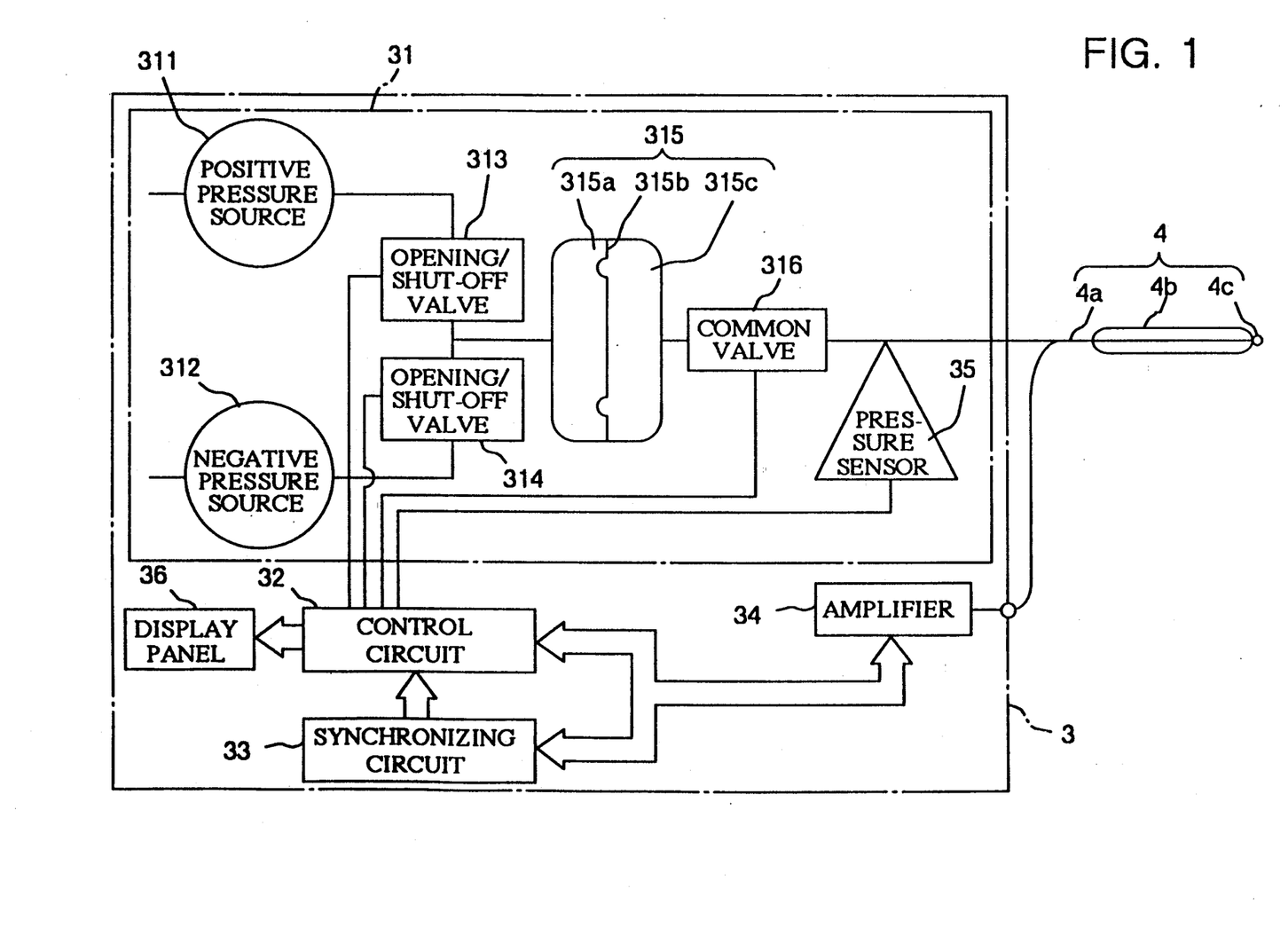
FIG. 1 is a block diagram illustrating the general features of the driver for operating the balloon pump.

Referring to FIG. 1, the features of the driver 3 according to a preferred embodiment of the present invention for operating the balloon pump 4 can be seen. The balloon pump 4 is equipped with a tube 4a that is connected to the driver 3, a balloon 4b that inflates and contacts within the aorata, and an arterial pressure sensor 4c that is located at the tip of the balloon 4b. In addition, the driver 3 includes a positive/negative pressure generator 31 which alternately supplies positive pressure and negative pressure to the balloon pump 4, an electronic controller 32, a blood pressure waveform synchronizing circuit 33, an arterial pressure waveform amplifier 34, a balloon pump pressure sensor 35, and a display panel 36.

In accordance with the preferred embodiment, the arterial pressure sensor 4c generates electrical signals that ar proportional to the magnitude of the arterial pressure inside the aorta. The arterial pressure sensor 4c can be as small as, for example, a particle of rice. The pressure sensor 35 is utilized in the zero point adjustment of the arterial pressure sensor 4c. This pressure sensor 35 is utilized because it is more reliable and more precise than the arterial pressure sensor 4c.

The positive/negative pressure generator 31 is equipped with a positive pressure source 311, a negative pressure source 312, a positive pressure opening/shut-off valve 313, a negative pressure opening/shut-off valve 314, an isolator 315, and a common valve 316. The isolator 315 has a primary chamber 315a, a secondary chamber 315c and a movable diaphragm or membrane 315b that separates the primary chamber 315a from the secondary chamber 315b. A sufficient amount of fluid is provided in the primary chamber 315a and the secondary chamber 315c to ensure proper operation of the system. In this example, helium gas is used as the gas that is supplied to the balloon pump 4.

The positive voltage opening/shut-off valve 313 and the negative pressure opening/shut-off valve 314 are connected to the primary chamber 315a. When the positive pressure opening/shut-off valve 313 is open and the negative pressure opening/shut-off valve 314 is closed, positive pressure will be directed from the positive pressure source 311 into the primary chamber 315a. As a result, the movable membrane 315b will move toward the secondary chamber 315c. During this period of time, if the common valve 316 is open, the balloon 4b on the balloon pump 4 will inflate.

In contrast, if the negative pressure opening/shut-off valve 314 is open and the positive pressure opening/shut-off valve 313 is closed, negative pressure will be directed from the negative pressure source 312 into the primary chamber 315a. If the common valve 316 is open during such period of time, the movable membrane 315b will move towards the primary chamber 315a. As a result, the balloon 4b on the balloon pump will contract or deflate. The positive pressure opening/shut-off valve 313, the negative pressure opening/shut-off valve 314, and the common valve 316 open and close as a result of the electronic controller that operates in accordance with signals output from the blood pressure waveform synchronizing circuit 33.

The pressure sensor 35 is attached to the tube 4a that connects the common valve 316 and the balloon pump 4 and the pressure sensor 35 detects the internal pressure of the balloon pump 4. The pressure sensor 35 is also connected to the electronic control circuit 32.

The arterial pressure sensor 4c, which is located on the tip of the balloon pump 4, is connected to the amplifier 34. The amplifier 34 amplifies the electrical signals, which have been detected and outputted by the arterial pressure sensor 4c, at the zero point set by the electronic control circuit 32. The signals, which have been amplified, are input into the blood pressure waveform synchronizing circuit 33 and the electronic control circuit 32. The blood pressure synchronizing circuit 33 determines the natural heartbeat from the signals output from the amplifier 34 and the blood pressure synchronizing circuit 33 outputs to the electronic control circuit 32 pulse signals that have been synchronized to the natural heartbeat. Additionally, the electronic control circuit 32 displays the arterial pressure on the display panel 36.

Figure 2A:
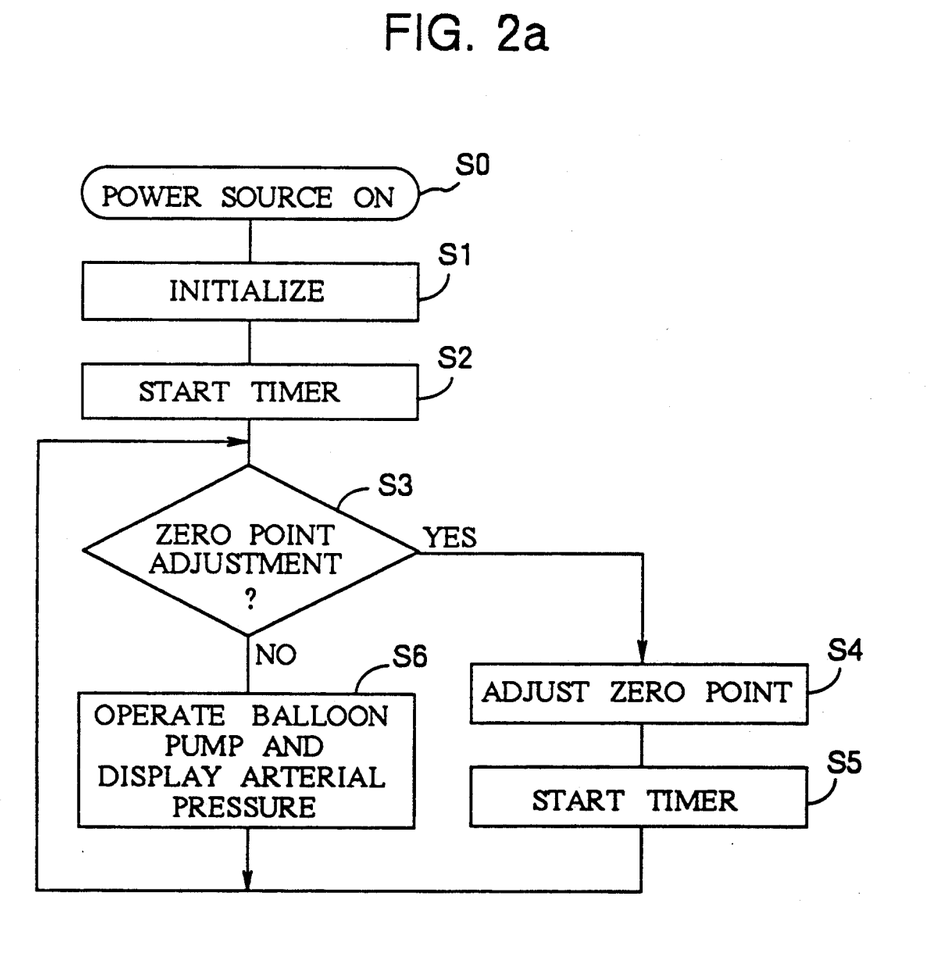
FIG. 2(a) is a flowchart illustrating the manner of operation of the electronic controller.

Reference is made to the flowchart depicted in FIG. 2(a) which illustrate the manner of operation of the electronic controller 32.

Turning initially to FIG. 2(a), if the power source of the electronic controller 32 is "on", the electronic controller 32 executes the steps starting with Step S0. Initially, the electronic controller 32 initializes each flag necessary for processing in later stages (Step S1). Next, the timer is started (Step S2).

By referring to the timer, the electronic controller 32 then determines whether it is time to make an adjustment to the zero point (Step S3). If it is determined that the prescribed time interval has passed, the electronic control circuit 32 carries out an adjustment of the zero point (Step 4). Thereafter, the timer is restarted in preparation for the next zero point adjustment (Step S5). If it is determined in (Step S3) that it is not time to make an adjustment, the electronic controller 32 operates the balloon pump 4 used in the treatment of the patient 1, and also displays the arterial pressure of the patient 1 (Step S6).

Figure 4:
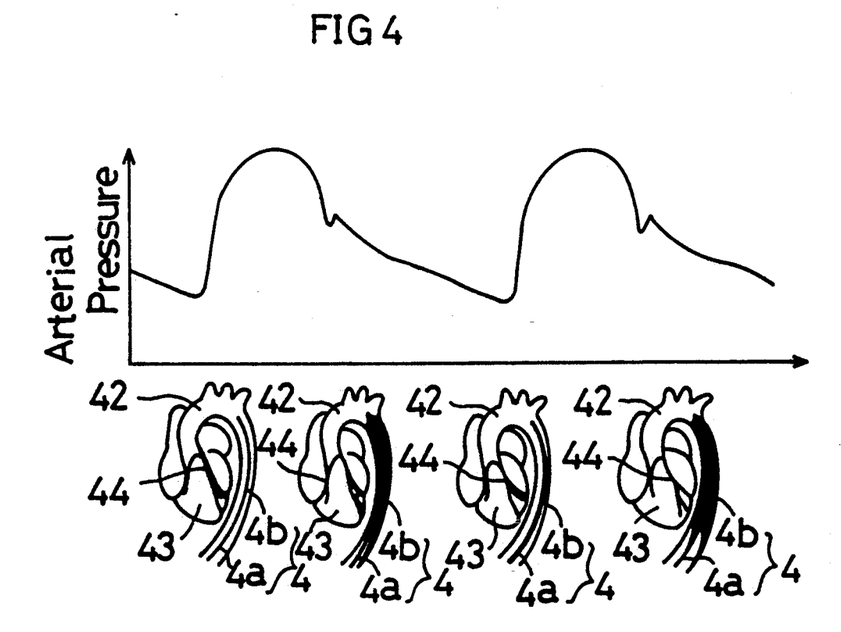
FIG. 4 is a graph illustrating the relationship between the arterial pressure and the inflation/contraction of the balloon pump.

To explain in general the operation/driving of the balloon pump that is performed in Step S6, reference is made to FIG. 4 which illustrates the relationship between the waveform of the arterial pressure and the inflation/contraction of the balloon pump 4.

The balloon pump 4 will be made to contract a few seconds before the arterial pressure rises, i.e., the heart contraction period. As a result of the contraction of the balloon pump 4, the arterial pressure of the aorta 42 drops, which means that blood can be easily pumped from the chambers of the heart 43. As a result, the blood flow rate increases at that time, and that aids in the recovery of the patient 1. After the peak in the arterial pressure has been observed, the balloon pump 4 is inflated after the prescribed period of time, i.e., at the time of expansion of the heart. As a result of the inflation of the balloon pump 4, the arterial pressure of the main section of the aorta 42 increases. In consequence, there is an increase in the amount of blood flowing to the coronary arteria 44. Thus, there is an added supply of oxygen and nutrients to the hearts, which aids in the recovery of a weakened heart.

As explained herein, at Step S6, the positive pressure opening/shut-off valve 313 and the negative pressure opening/shut-off valve 314 alternately close in response to the beats of the heart that are detected by the blood pressure waveform synchronizer. As a result, the balloon pump 4 inflates and contracts.

Moreover, at Step S6, at the same time as the inflation and contraction of the balloon pump 4, there is a display of the arterial pressure on the display panel 36. The patient 1 can be treated as the physician observes the arterial pressure displayed on the display panel 36.

Figure 2B:
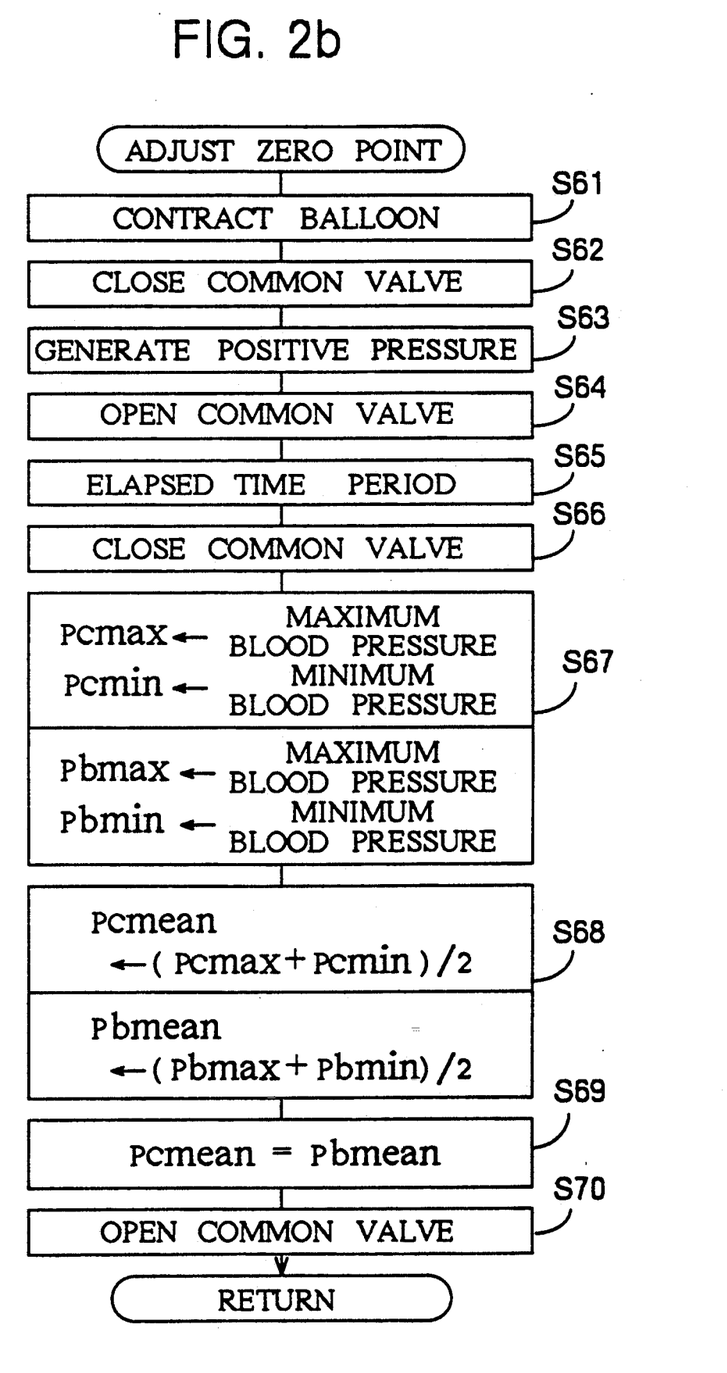
FIG. 2(b) is a flowchart illustrating the manner in which the zero point is adjusted.
Figure 2C:
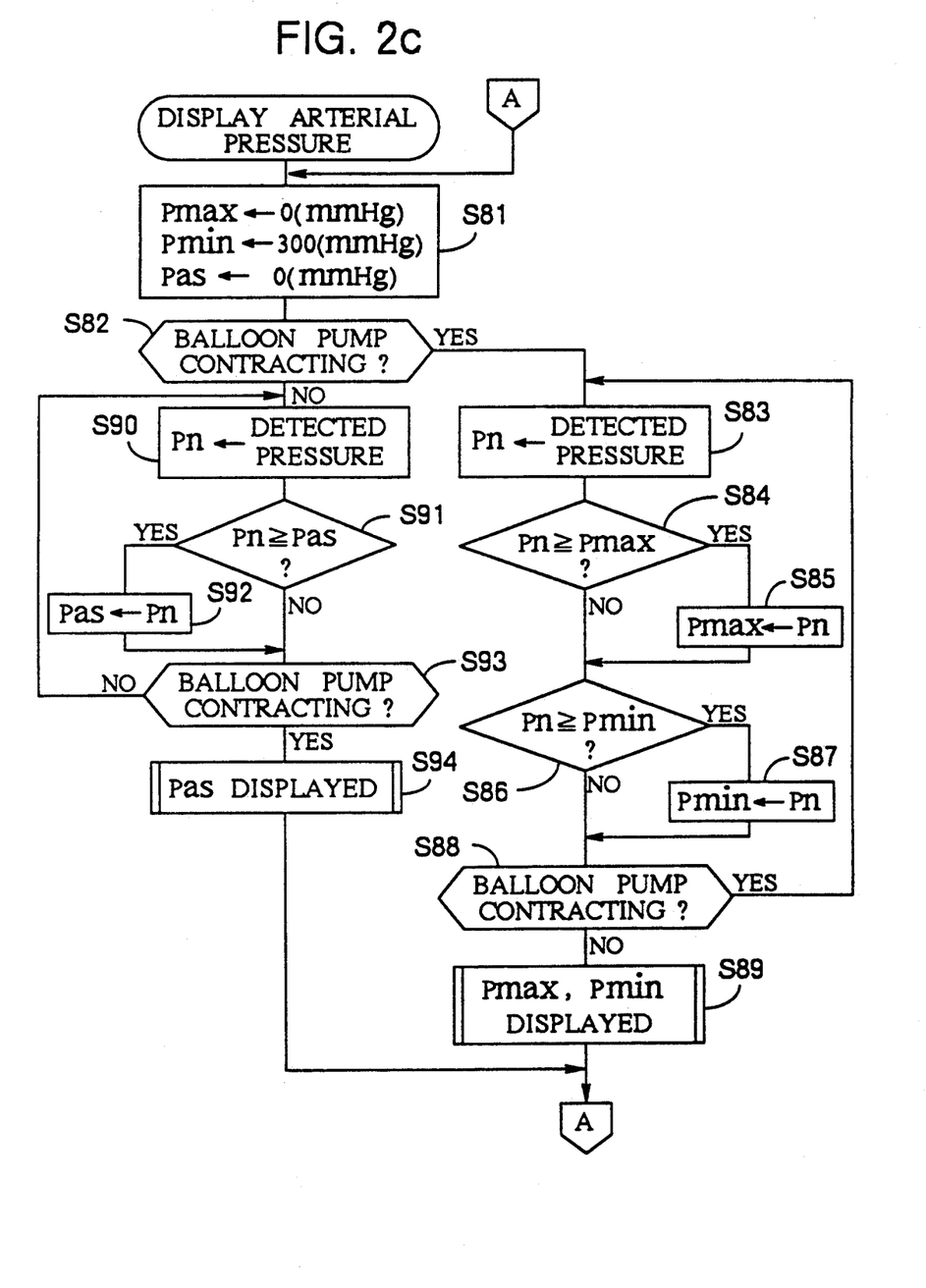
FIG. 2(c) is a flowchart illustrating the manner of operation of the display panel.

With reference to FIG. 2(c), an explanation will be provided of how the arterial pressure is displayed on the display panel 36.

First, the initial settings for the registers Pmax, Pmin, and Pas are set (Step S81). The register Pmax records the maximum blood pressure for the natural heart. The register Pmin records the minimum blood pressure for the natural heart. The register Pas records the assist pressure resulting from the balloon pump 4.

At Step S82, a determination is made as to whether the balloon pump 4 is contracting. If the balloon pump 4 is contracting (Yes), the arterial pressure detected by the arterial pressure sensor 4c will be stored in register Pn (Step S83).

Thereafter, the steps necessary for determining the maximum blood pressure (Steps S84, S85, and S88) and the steps necessary for determining the minimum blood pressure (Steps S86, S87, and S88) for a natural heart are carried through. The maximum blood pressure and the minimum blood pressure are then displayed.

If the balloon pump 4 is inflating at Step S82 (No), the arterial pressure, which has been detected by the arterial pressure sensor 4c, will be stored in register Pn (Step S90). Thereafter, the maximum blood pressure while the balloon pump 4 is inflating will be found, i.e., the steps (Steps S91, S92, and S93) for finding the assist pressure of the balloon pump 4 will be carried through. The assist pressure that is found is then displayed on the display panel 36 (Step S94).

As a result of the steps explained above, the maximum blood pressure and the minimum blood pressure of the natural heart as well as the assist pressure of the balloon pump 4 are displayed on the display panel 36 and synchronized with the inflation/contraction of the balloon pump 4.

The zero point on the arterial pressure sensor 4c fluctuates because of several reasons. If the fluctuation of the zero point is slight, error contained in the display of the arterial pressure will be minimal. Therefore, there will be little, if any, problems related to the treatment of the patient 1. If, however, the fluctuation in the zero point on the arterial pressure sensor 4c is large, the physician will not be able to accurately assess how the patient 1 is progressing. For that reason, it is desirable that the zero point of the sensor be adjusted before the fluctuation in the zero point of the arterial pressure sensor 4c becomes large.

In the preferred embodiment of the present invention, the focus is on the fact that the zero point gradually fluctuates as time elapses and that at each prescribed interval of time, the zero point of the arterial pressure sensor 4c is adjusted.

An explanation of what is involved in the adjustment of the zero point at Step S4 in FIG. 2(a) can be understood by referring to FIG. 2(b).

Initially, the balloon pump 4 is subjected to negative pressure, and, as a result, the balloon pump 4 contracts (Step S61). As soon as the contraction of the balloon pump 4 is completed, the common valve 316 closes (Step S62). Thereafter, the electronic controller 32 opens the positive pressure opening/shut-off valve 313, which subjects the isolator 315 to positive pressure (Step S63). During that time, positive pressure acts upon the isolator 315. However, since the common valve 316 is closed, the balloon pump 4 remains in its contracted state. Unless the pressure in the isolator 315 should change, the electronic controller 32 will close the opening/shut-off valve 313. Since the pressure of the positive pressure source 311 and the capacity of the isolator 315 are constant, a constant amount of air will be stored within the isolator 315.

After that, the electronic controller 32 opens the common valve 316 (Step S64). The opening of the common valve 316 enables the correct amount of gas to be supplied to the balloon 4. At that time, the balloon 4b on the balloon pump 4, which is substantially completely contracted, will inflate moderately. The balloon 4b will not be allowed to inflate to its fullest extent so as to avoid having the balloon 4b close off the aorta. Therefore, while the balloon 4b is inflating moderately, blood will be flowing within the aorta.

When the prescribed period of time has elapsed (Step S65), the electronic controller 32 will acknowledge that the internal pressure of the balloon pump 4 has stabilized and will close the common valve 316 (Step S66).

As soon as the common valve 316 is closed, the inner part of the balloon pump 4 will likewise close. As a result, the internal pressure of the balloon pump 4 will be about equal to the arterial pressure to which the balloon 4b is subjected.

In this state, the electronic controller 32 evaluates, at the same time, the arterial pressure measured by the arterial pressure sensor 4c and the pressure measured by the pressure sensor 35 during a period of approximately one second (Step S67). Simultaneously, the electronic controller 32 records into the register Pcmax the maximum arterial pressure value that has been measured by the arterial pressure sensor 4c and records into the register Pcmin the minimum arterial pressure value that has been measured by the arterial pressure sensor 4c. In addition, the electronic controller 32 records into the register Pbmax the maximum arterial pressure value that has been measured by the pressure sensor 35 and records into the register Pbmin the minimum arterial pressure value that has been measured by the pressure sensor 35.

Figure 5:
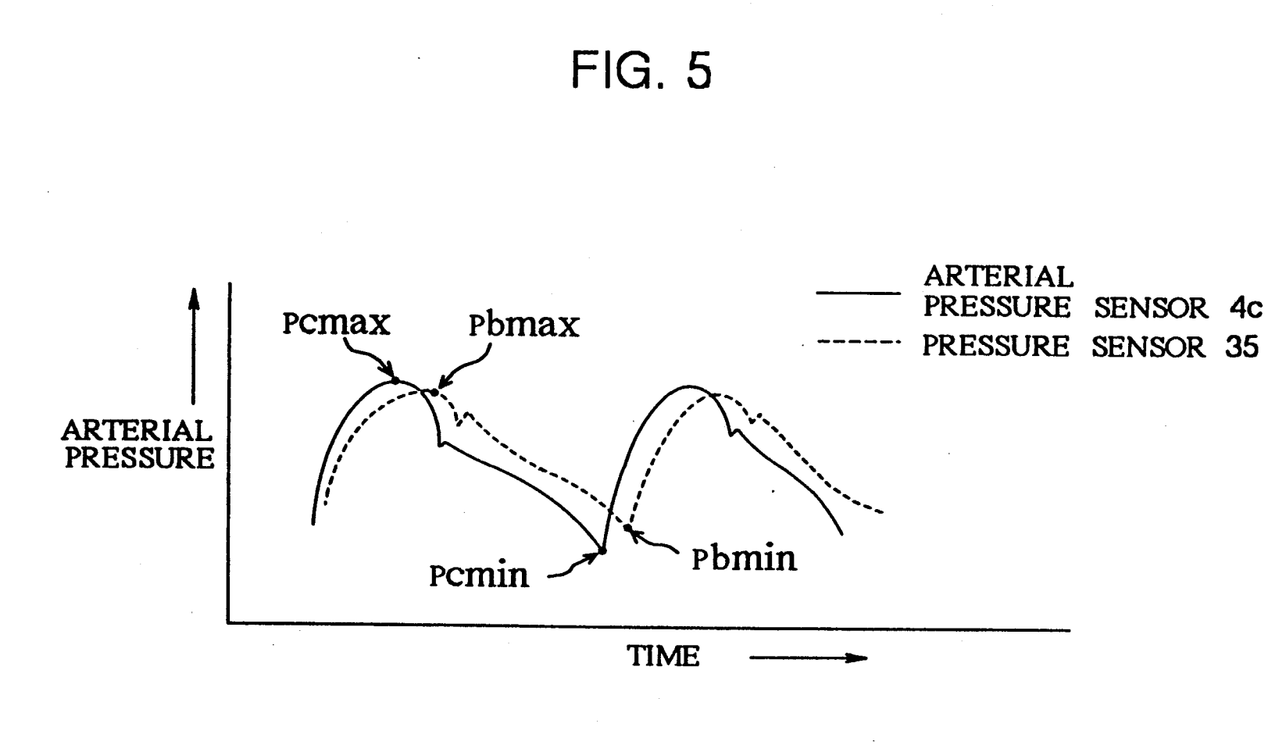
FIG. 5 is a graph illustrating the relationship between the pressure measured by the arterial pressure sensor and the pressure measured by the pressure sensor positioned away form the aorta.

A typical example of the data that is measured at that time is provided in FIG. 5. As is shown in this example, the arterial pressure waveform, measured by the arterial pressure sensor 4c, does not necessarily coincide with the arterial pressure waveform obtained by the pressure sensor 35. This is because the pressure sensor 35 is positioned in a spot that is far away from the aorta.

The electronic controller 32 calculates the mean value of the arterial pressure (i.e., the mean value of the maximum value and the minimum value of the arterial pressure waveform) which has been measured by the arterial pressure sensor 4c, and records that value in the register Pcmean (Step S68). Moreover, at the same time, the electronic controller 32 records the mean value for the arterial pressure which has been measured by the pressure sensor 35 and records that value in the register Pbmean.

After that, the zero point will be computed to compensate for the difference between the mean value in the register Pcmean and the value in the register Pbmean, and the zero point in the amplifier 34 will be adjusted so that the value in the register Pc mean and the value in the register Pbmean will be equal (Step S69).

When the adjustment of the zero point is completed, the electronic controller 32 opens the common valve 316 and the process is finished.

As has been explained herein, with the device according to the present invention, the zero point in the arterial pressure sensor 4c is automatically adjusted in accordance with the arterial pressure detected by the pressure sensor 35 each time that a prescribed period of time has elapsed. The zero point in the arterial pressure sensor 4c is adjusted during the treatment of a patient and therefore, the arterial pressure will always be accurately displayed on the display panel 36. Additionally, the adjustment of the zero point is carried out completely automatically so that physicians will be able to give their undivided attention to the treatment of the patient 1.

The device according to the present invention is advantageous in that it enables the adjustment of the zero point of an arterial pressure sensor while the arterial pressure sensor remains inserted in the aorta. Therefore, the zero point of the arterial pressure sensor can be adjusted while the balloon pump is being used in the treatment of a patient.

The principles, preferred embodiments and modes of operation of the present invention have been described in the foregoing specification. However, the invention which is intended to be protected is not to be construed as limited to the particular embodiments disclosed. Further, the embodiments described herein are to be regarded as illustrative rather than restrictive. Variations, changes and equivalents may be made by others without departing from the spirit of the present invention. Accordingly, it is expressly intended that all such variations, changes and equivalents which fall within the spirit and scope of the present invention as defined in the claims, be embraced thereby.

What is claimed is:

1. A device including an intra-aortic balloon pump and means for operating the intra-aortic balloon pump, said intra-aortic balloon pump having an arterial pressure sensor associated therewith for measuring arterial pressure, said means or operating comprising:
   a balloon pump pressure sensor for measuring an internal pressure of the intra-aortic balloon pump;
   means for applying a positive pressure to provide gas to the intra-aortic balloon pump sufficient to inflat the intra-aortic balloon pump; and
   adjustment mean for comparing an arterial pressure measured by the arterial pressure sensor with the internal pressure of the intra-aortic balloon pump as measured by the balloon pump pressure sensor and for adjusting a zero point of said arterial pressure sensor to eliminate differences between the arterial pressure measured by the arterial pressure sensor and the internal pressure measured by the balloon pump pressure sensor.

2. The device in accordance with claim 1, including an isolator fluidly connected to said means for applying a positive pressure, said isolator including a primary chamber nd a secondary chamber separated from one another by a diaphragm.

3. The device in accordance with claim 2, including means fluidly connected to the isolator for applying a negative pressure sufficient to contract the balloon pump.

4. The device in accordance with claim 3, including a positive pressure opening/shut-off valve positioned between the means for applying positive pressure and the isolator, and including a negative opening/shut-off valve positioned between the means for applying negative pressure and the isolator.

5. The device in accordance with claim 3, including a common valve positioned between and connected to the isolator and the balloon pump.

6. The device in accordance with claim 1, including display means for displaying a maximum blood pressure, a minimum blood pressure and an assist blood pressure associated with operation of the balloon pump.

7. A method of operating a balloon pump positioned in a body of a patient wherein the balloon pump has an arterial pressure sensor positioned at an end thereof for measuring arterial pressure, the method comprising the steps of:
   contacting the balloon pump prior to when arterial pressure rises;
   inflating the balloon pump after the arterial pressure has reached a maximum value;
   determining the arterial pressure through use of the arterial pressure sensor;
   adjusting the zero point of the arterial pressure sensor at predetermined time intervals while the balloon pump is positioned in the patient's body.

8. The method according to claim 7, wherein the step of adjusting the zero point includes the step of determining an internal pressure of the balloon pump through use of a balloon pump pressure sensor.

9. The method according to claim 8, wherein the step of adjusting the zero point of the arterial pressure sensor includes the steps of determining the mean of a maximum and a minimum blood pressure measured by the arterial pressure sensor, determining the mean of a maximum and a minimum pressure measured by the balloon pump pressure sensor, and computing the zero point of the arterial pressure sensor to compensate for differences between the means of the maximum and minimum pressures measured by the arterial pressure sensor and the mean of the maximum and minimum pressures measured by the balloon pump pressure sensor.

10. The method according to claim 9, including the steps of, at said predetermined time interval, contracting the balloon and closing a common valve that is positioned between balloon pump and an isolator which is connected to positive and negative pressure sources.

11. The method according to claim 10, including, after the common valve has been closed, the steps of, generating a positive pressure and opening the common valve or a predetermined period of time to inflate the balloon pump.

* * * * *